United States Patent [19]

Stahly et al.

[11] Patent Number: 4,502,995

[45] Date of Patent: * Mar. 5, 1985

[54] NUCLEOPHILIC SUBSTITUTION PROCESS

[75] Inventors: Barbara C. Stahly; G. Patrick Stahly, both of Baton Rouge, La.

[73] Assignee: Ethyl Corporation, Richmond, Va.

[*] Notice: The portion of the term of this patent subsequent to Jan. 25, 2000 has been disclaimed.

[21] Appl. No.: 452,518

[22] Filed: Dec. 23, 1982

Related U.S. Application Data

[63] Continuation-in-part of Ser. No. 317,321, Nov. 2, 1981, Pat. No. 4,370,278.

[51] Int. Cl.$^3$ .................. C07C 121/50; C07C 63/33
[52] U.S. Cl. ............................. 260/465 G; 562/492
[58] Field of Search ................. 260/465 G; 562/492

[56]  References Cited

U.S. PATENT DOCUMENTS

| | | | |
|---|---|---|---|
| 3,755,427 | 8/1973 | Adams et al. | 562/492 |
| 3,920,839 | 11/1975 | Wasley | 424/319 |
| 3,959,364 | 5/1976 | Armitage | 562/492 |
| 4,239,901 | 12/1980 | Rainer | 560/34 |
| 4,278,516 | 7/1981 | Zaiko et al. | 204/158 HA |

OTHER PUBLICATIONS

Golinski et al., Tetrahedron Letters No. 37, pp. 3495–3498, (1978).
Mokosza et al., J. Org. Chem., vol. 45, pp. 1534–1535, (1980).
Mokosza, Int. Conf. Chem. Biotechol. Biol. Act. Nat. Prod. (Proc.), vol. 2, pp. 480–490, (1981).

*Primary Examiner*—Delbert R. Phillips
*Attorney, Agent, or Firm*—Donald L. Johnson; John F. Sieberth; Patricia J. Hogan

[57] ABSTRACT

Fluoronitrolarylacetonitriles are prepared by reacting a fluoronitroaromatic compound having a nitro substituent, at least one fluoro substituent, and at least one replaceable hydrogen on (1) a benzene ring bearing at least one other innocuous substituent, (2) a heterocyclic aromatic ring, or (3) a carbocyclic aromatic ring of a polycyclic ring structure with an alpha,alpha-disubstituted acetonitrile in an inert solvent and in the presence of a base so that the nitrile undergoes a nucleophilic substitution on an unsubstituted ring carbon of the fluoronitroaromatic compound during which an alpha-substituent functions as a leaving group.

11 Claims, No Drawings

NUCLEOPHILIC SUBSTITUTION PROCESS

CROSS-REFERENCE

This application is a continuation-in-part of copending application Ser. No. 317,321, filed Nov. 2, 1981, now U.S. Pat. No. 4,370,278.

TECHNICAL FIELD

This invention relates to processes for preparing fluoronitroarylacetonitriles and derivatives thereof.

BACKGROUND

There are known techniques of preparing profen-type pharmaceuticals and other materials having a relatively complex aryl group attached to the alpha-carbon of a substituted or unsubstituted acetic acid. For example, U.S. Pat. Nos. 3,755,427 (Adams et al.), 3,959,364 (Armitage et al.) and 4,278,516 (Zaiko et al.) disclose processes for converting various starting materials into flurbiprofen, i.e., 2-(2-fluoro-4-biphenylyl)propionic acid, and similar compounds having anti-inflammatory, analgesic, and antipyretic properties; Carney et al., "A Potent Non-Steroidal Anti-Inflammatory Agent: 2-[3-Chloro-4-(3-pyrrolinyl)phenyl]propionic Acid," *Experientia*, Vol. 29, page 938 (1973) teach, inter alia, the preparation of their anti-inflammatory agent—also known as pirprofen—via an ethyl 2-(3-chloro-4-nitrobenzene)propionate intermediate; U.S. Pat. No. 4,239,901 (Rainer) shows that pyrazol-1-ylphenyl and pyrazolin-1-ylphenylacetic acids having anti-inflammatory properties can be synthesized from various intermediates, including polychloronitrobenzeneacetic acid esters; and it is known that indoprofen, i.e., 2-[4-(1,3-dihydro-1-oxo-2H-isoindol-2-yl)phenyl]propionic acid, and indobufen, i.e., 2-[4-(1,3-dihydro-1-oxo-2H-isoindol-2-yl)phenyl]butyric acid, can be prepared from the appropriate 2-(4-nitrobenzene)-alpha-alkylacetic acids.

Nitroarylacetic acids and their esters and nitriles, as well as the amino derivatives thereof, have been found to be particularly useful intermediates for the synthesis of these pharmaceuticals and other materials. however, in the past, a disadvantage of employing them as chemical intermediates has been the difficulty of preparing them by conventional techniques. Even the preferred procedures for preparing them have proven to be difficult, tedious, and time-consuming, as evidenced by Example 23 of U.S. Pat. No. 3,868,391 (Carney et al. II) and Example 16 of Rainer, both of which show the use of days of refluxing to accomplish only a portion of their syntheses.

It would obviously be a welcome contribution to the art to provide a method of synthesizing fluoronitroarylacetonitriles and derivatives thereof in a simple and straightforward manner. A method of synthesizing certain of these compounds, i.e., 2-(fluoronitrobenzene)acetonitriles and derivatives thereof, is disclosed in the above-identified parent of the present application, which teaches that the 2-(fluoronitrobenzene)acetonitriles and derivatives may be prepared from fluoronitrobenzenes and alpha-substituted alkyl cyanides by a nucleophilic substitution reaction in a substantially anhydrous aprotic solvent and in the presence of a base.

STATEMENT OF INVENTION

An object of this invention is to provide processes for preparing fluoronitroarylacetonitriles in moderate-to-good yield with high selectivity in a simple and straightforward manner.

Another object is to provide novel, improved processes for preparing derivatives of the nitriles.

These and other objects are attained by (I) reacting (A) a fluoronitroaromatic compound having a nitro substituent, at least one fluoro substituent, and at least one replaceable hydrogen on (1) a benzene ring bearing at least one other innocuous substituent, (2) a heterocyclic aromatic ring, or (3) a carbocyclic aromatic ring of a polycyclic ring structure with (B) an alpha,alpha-disubstituted acetonitrile in an inert solvent and in the presence of a base so that the nitrile undergoes a nucleophilic substitution on an unsubstituted ring carbon of the fluoronitroaromatic compound during which an alpha-substituent functions as a leaving group, thereby forming a fluoronitroarylacetonitrile and (II) when appropriate, converting the fluoronitroarylacetonitrile to a desired derivative thereof.

DETAILED DESCRIPTION

Fluoronitroaromatic compounds utilizable in the practice of the invention include a variety of such compounds—the chief requirements for their utility being that (1) they bear at least one ar-nitro and at least one ar-fluoro substituent, (2) they contain at least one replaceable hydrogen on an aromatic ring to which a nitro group and a fluoro substituent ae attached, (3) they be devoid of substituents which would interfere with the desired nucleophilic substitution reaction, and (4) when the aromatic ring bearing the required nitro and fluoro substituents and a replaceable hydrogen is a benzene ring, they bear at least one innocuous ar-substituent, i.e., an ar-substituent other than a halo substituent that does not interfere with the desired nucleophilic substitution reaction.

Thus, the utilizable fluoronitroaromatic compounds include compounds having one or more simple or fused aromatic rings containing five or six members and either bearing no substituents other than the required nitro and fluoro substituents (when the aromatic ring bearing those substituents is a ring other than a benzene ring) or also bearing any of a variety of innocuous substituents, such as nitro, alkyl, alkoxy, alkylmercapto, trifluoromethyl, dialkylamino, dialkanoylamino, cyano, dialkylcarbamoyl, alkylsulfonyl, dialkylsulfamoyl, alkoxyalkyl, haloalkyl, cycloalkyl, halocycloalkyl, etc.—any alkyl chains in the substituents generally being lower alkyl chains. ("Lower alkyl" is used in this specification in its usual sense to refer to an alkyl group containing up to about 6 carbons.)

As indicated above, the ring bearing the required nitro and fluoro substituents must bear at least one other innocuous substituent when it is a benzene ring, but such innocuous substituents are optional when the ring is an aromatic ring other than a benzene ring. When the fluoronitroaromatic compound has a polycyclic ring structure, any such innocuous substituent may be on the same ring as the ring bearing the nitro and fluoro substituents and/or on a ring which is directly or indirectly attached to the ring bearing the nitro and fluoro substituents.

When the aromatic ring bearing the required nitro and fluoro substituents is a six-membered ring, there will be at least one replaceable hydrogen in a position para or ortho to the carbon bearing the nitro substituent; and it is preferred that there be a replaceable hydrogen in the para position. Fluoronitroaromatic compounds having a five-membered ring should have a replaceable hydrogen on a carbon adjacent to, or separated by two ring atoms from, the carbon bearing the nitro substituent.

Exemplary of fluoronitroaromatic compounds that may be used in the practice of the invention are (A) heterocyclic compounds which preferably contain five- or six-membered rings having aromatic character, such as the various fluoro-substituted nitropyridine-N-oxides, nitroquinolines, nitroisoquinolines, and nitrothiophenes, etc., (B) fused-ring aromatic compounds, such as the various fluoro-substituted nitronaphthalenes, nitroindoles, etc., (C) aromatic compounds containing a plurality of simple rings, such as the various fluoro-substituted nitrobiphenyls, benzylnitrobenzenes, pyridylnitrobenzenes, nitrodiphenyl ethers, etc., and (D) aromatic compounds containing a single simple ring, such as the various fluoro-substituted nitrotoluenes, dimethylnitrobenzenes, diethylnitrobenzenes, dibutylnitrobenzenes, dinitrobenzenes, di- and trinitrotoluenes, nitro-N,N-diethylanilines, nitro-N-ethylacetanilides, nitrobenzylcyanides, and nitrophenyl acetates, etc.—in each case bearing one or more ar-fluoro substituents and having at least one replaceable hydrogen in an appropriate position.

When the fluoronitroaromatic compound is a fluoronitrobenzene, it preferably has a fluoro substituent in a position ortho to a nitro substituent. Also, regardless of the particular type of fluoronitroaromatic compound, it preferably has a replaceable hydrogen in a position para to a nitro group, since the nucleophilic substitution reaction of the invention tends to be highly selective on the para position, and the use of such compounds therefore leads to the production of fluoronitroarylacetonitriles which are ideally suited for the synthesis of compounds of the same general type as the anti-inflammatory agents described in the aforementioned references.

In some cases, polynitroaromatic reactants may undergo substitution reactions whereby one of the nitro groups is replaced by the nitrile reactant. Therefore, the possibility of this competitive reaction should be kept in mind when selecting a polynitroaromatic for use in the process.

The alpha,alpha-disubstituted acetonitriles that can be used in the practice of the invention also include a variety of such compounds, which—in general—may be represented by the formula:

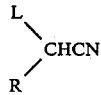

wherein L is a leaving group and R is halo (preferably chloro) or, more preferably, a hydrocarbyl (e.g., alkyl, alkenyl, alkynyl, cycloalkyl, cycloalkenyl, aryl, aralkyl, etc.) or hydrocarbyloxyhydrocarbyl (e.g., alkoxyalkyl, aryloxyalkyl, alkoxyaryl, alkoxycycloalkyl, etc.) group which most preferably contains up to about 10 carbons.

Exemplary leaving groups, L, include halo, aryloxy, haloaryloxy, alkylthio, cycloalkylthio, arylthio, aralkylthio, haloalkylthio, halocycloalkylthio, haloarylthio, haloaralkylthio, or, less preferably, alkoxy, cycloalkoxy, aralkoxy, haloalkoxy, halocycloalkoxy, haloaralkoxy, and the like, as well as other suitable leaving groups which have been described in the literature, e.g., in Golinski et al., "'Vicarious' Nucleophilic Substitution of Hydrogen in Aromatic Nitro Compounds, *Tetrahedron Letters*, Vol. 37, pp. 3495–8 (1978) and in Makosza et al., "Vicarious Substitution of Hydrogen in Aromatic Nitro Compounds with Acetonitrile Derivatives," *Journal of Organic Chemistry*, Vol. 45, pp. 1534–5 (1980).

When the leaving group is an organic group, it is generally preferred that it contain not more than about 10 carbons, although organic leaving groups having an even higher carbon content are satisfactory in the practice of the invention. Preferably, the leaving group is halo, i.e., chloro, bromo, fluoro, or iodo; and it is more preferably chloro or bromo, most preferably chloro.

A few examples of alpha,alpha-disubstituted acetonitriles that can be used in the practice of the invention are 2-chloropropionitrile, 2-chlorobutyronitrile, 2-chlorovaleronitrile, 2-chlorocapronitrile, 2-chloro-4-pentenenitrile, 2-chloro-3,3-dimethyl-butyronitrile, 2-chloro-2-phenylacetonitrile, 2-chloro-2-cyclohexylacetonitrile, 2-chloro-3-(3-chloro-o-tolyl)propionitrile, 2-chloro-3-phenylpropionitrile, the corresponding bromo and iodo compounds, and the like. The alpha-halo-alpha-hydrocarbylacetonitriles, i.e., alpha-haloalkyl cyanides containing at least three carbons—particularly 2-chloropropionitrile and 2-bromopropionitrile—are especially preferred, although similar cyanides in which the alpha-halo substituent is replaced by one of the other leaving groups mentioned above are also highly desirable.

In another highly desirable embodiment of the invention, the alpha,alpha-disubstituted acetonitrile is an alpha,alpha-dihaloacetonitrile, most preferably an alpha,alpha-dichloroacetonitrile, which leads to the formation of a product having a reactive halo substituent in the alpha-position, e.g., a product corresponding to the formula:

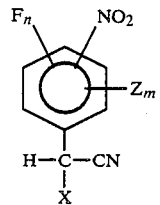

wherein X is halo, preferably chloro; Z is an innocuous substituent; and m and n are intergers of at least 1. Such products enable facile synthesis of a variety of end products. Most preferably the nitro group is in the position para to the nitrile substituent, although it may be located in an ortho position.

The solvent used in a nucleophilic substitution process of the invention may be any solvent that is inert under the conditions of the reaction, i.e., any solvent that will not prevent the reaction from occurring. Such solvents are substantially anhydrous and are generally aprotic, although solvents such as liquid ammonia are also utilizable.

Illustrative aprotic solvents which may be employed in the process of the invention include ethers such as diethyl ether, dibutyl ether, 1-ethoxyhexane, tetrahydrofuran, 1,4-dioxane, 1,3-dioxolane, diglyme, 1,2-diethoxyethane, anisole, etc.; tertiary amines such as pyridine, N-ethylpiperidine, triethyl amine, tributyl amine, N,N-diphenyl-N-methyl amine, N,N-dimethylaniline, etc., and other solvents. However, the preferred aprotic solvents are dipolar aprotic solvents such as dimethyl sulfoxide, N,N-dimethylformamide, N,N-dimethylacetamide, dimethyl sulfone, tetramethylene sulfone, N-methylpyrrolidinone, and the like.

Bases useful in the practice of the invention include all bases strong enough to activate the nitrile reactant, e.g., alkaline earth metal compounds such as calcium oxide, calcium hydride, calcium hydroxide, barium oxide, barium hydroxide, magnesium hydroxide, zinc hydroxide, etc. However, the base is preferably an alkali metal compound, e.g., an organoalkali metal compound, alkali metal hydride, alkali metal hydroxide, alkali metal oxide, alkali metal amide, or alkali metal alcoholate, such as butyllithium, phenyllithium, ethylsodium, amylsodium, butylpotassium, benzylpotassium, sodium dimsylate (i.e., the sodium salt of diethylsulfoxide), sodium hydride, potassium hydride, sodium hydroxide, potassium hydroxide, sodium oxide, potassium oxide, sodium amide, potassium amide, lithium diisopropylamide, aodium methoxide, potassium t-butoxide, the sodium salt of the monomethylether of ethylene glycol, sodium phenoxide, and the like. Ordinarily the use of sodium hydride or potassium hydride will be found most convenient and economical.

Use of an alkali metal compound as the base permits the alternatives of using the alkali metal compound alone or in conjunction with a phase transfer catalyst, such as a quaternary ammonium salt, ethylene glycol, or a suitable crown ether. When a phase transfer catalyst is employed (1) the alkali metal compound may be any of the alkali metal compounds generically or specifically indicated above, although the type of alkali metal compound being used determines the type of crown ether that is preferably utilized—lithium bases generally calling for the use of a 12-crown-4 ether, sodium bases usually calling for the use of a 15-crown-5 ether, and potassium bases generally calling for the use of an 18-crown-6 ether, and (2) the reaction medium may be any of the aprotic solvents mentioned above, or it may be an inert liquid hydrocarbon such as benzene, toluene, xylene, hexane, heptane, isooctane, or the like.

When an alkali metal hydride, especially a highly pure alkali metal hydride, is employed as the base, it is desirable to include a small amount of a transfer agent such as water, alcohol, or the like in the system. It is believed that the transfer agent activates the hydride by reacting therewith to form a small amount of the alkali metal hydroxide or alcoholate.

The fluoronitroarylacetonitrile synthesis of the invention is conducted in a substantially anhydrous reaction system, and accordingly, except when a small amount of water (which is itself consumed by reaction with the alkali metal hydride) is employed as a transfer agent, the components of the reaction system should be brought together and maintained under a dry inert atmosphere. Thus, while it is possible to conduct the process in the presence of air, it is desirable to maintain the reaction system under an atmosphere of dry nitrogen or the like. Since the reaction itself is normally an exothermic reaction, with its initiation readily ascertainable by noting the exotherm produced, the reactants are ordinarily brought together at ambient temperatures, although the temperature may be raised or lowered to suit the needs of the occasion if desired.

The fluoronitroaromatic compound and alpha,alpha-disubstituted acetonitrile may be used in amounts such as to provide a stoichiometric excess of either of the reactants or the stoichiometric amount of each. However, when a stoichiometric excess of the fluoronitroaromatic compound is employed, the quantity of product obtainable will be limited by the quantity of nitrile used, so, it is desirable to utilize a stoichiometric excess of the nitrile. The amount of base employed is preferably such as to provide at least two molar equivalents of base per mol of fluoronitroaromatic compound, since the use of smaller amounts—although permitting the reaction to occur—makes the base the limiting reagent.

The mode of addition of the ingredients of the reaction system is not particularly critical. Accordingly, it is convenient to add the fluoronitroaromatic compound to a mixture of the other materials, add the base to a mixture of the other materials, add the reactants to a mixture of the base and solvent, introduce all four ingredients simultaneously into the reaction zone, or the like. Since the reaction ordinarily proceeds very rapidly, long reaction times are not required. The reaction will usually be completed within a matter of minutes or a few hours at ambient temperatures.

When derivatives of the fluoronitroarylacetonitriles are desired, they may be prepared by employing conventional techniques to convert to the desired derivatives the fluoronitroarylacetonitriles made in accordance with the present invention. Thus, for example:

(A) 2-(3-fluoro-6-methyl-4-nitrobenzene)propionitrile synthesized by the process of the invention may be reduced to 2-(4-amino-3-fluoro-6-methylbenzene)propionitrile, converted into 2-(2-fluoro-6-methylbiphenyl)propionitrile by means of a Gomberg-Bachmann reaction with benzene, and then converted into 2-(2-fluoro-6-methylbiphenylyl)propionic acid and (B) 2-(3-fluoro-4-nitronaphthalene)butyronitrile synthesized by the process of the invention may be hydrolyzed to 2-(3-fluoro-4-nitronaphthalene)butyric acid and subsequently reduced to 2-(4-amino-3-fluoronaphthalene)butyric acid, etc.

The particular conventional techniques used to convert the fluoronitroarylacetonitriles into their various derivatives are not critical. It may sometimes be desirable to use certain particular techniques for the preparation of the derivatives, e.g., (a) the reduction and/or hydrolysis techniques taught in March, *Advanced Organic Chemistry*, McGraw-Hill, New York, 1977, pages 809–10, 1125–6, and the references cited therein; and (b) the Gomberg-Bachmann techniques taught in March, pages 653–4, and in *Organic Reactions*, Vol. 2, page 224 (1944); *Journal of the American Chemical Society*, Vol. 46, page 2339 (1924); *Chemical Rev.*, Vol. 57, page 77 (1957); and *Journal of the Chemical Society*, Vol. D 1971, page 411, the disclosures of all of which are incorporated herein by reference. However, the overall processes for preparing the derivatives are simplified and made more efficient and economical by the present simplification of the synthesis of the fluoronitroarylacetonitriles regardless of the particular techniques used to convert them into their various derivatives.

As indicated above, the present invention is particularly advantageous in providing a readier and more economical route to the synthesis of chemical products that can be prepared from fluoronitroarylacetonitriles, e.g., products of the type disclosed in U.S. Pat. Nos. 3,641,040, 3,657,230, 3,767,805, 3,868,391, 3,936,467, 3,933,763, 3,997,669, 4,010,274, 4,118,504, 4,126,691, 4,163,788, and 4,239,901, agricultural chemicals, etc.

The following example is given to illustrate the invention and is not intended as a limitation thereof.

EXAMPLE

Into a flame-dried flask under nitrogen were placed 140 mg (1.2 mmols) of potassium t-butoxide and 1 ml of N,N-dimethylformamide (DMF), and the resulting solution was cooled in an ice water bath. A solution of 142 mg (0.68 mmol) of 4-fluoro-3-nitrobenzotrifluoride and 60 mg (0.67 mmol) of 2-chloropropionitrile in 0.5 ml of DMF was added dropwise to the cold base solution. The resulting purple mixture was allowed to react for 15 minutes at 0°–5° C. and was then poured into 20 ml of 1N HCl. The aqueous mixture was extracted with three 20 ml portions of diethyl ether, and the ether layers were combined, dried over magnesium sulfate, and stripped to give an oil which, after preparative thin layer chromatography, afforded 32 mg of an approximately 1/1 mixture of 2-(2-trifluoromethyl-4-nitro-5-fluorobenzene)propionitrile and 2-(2-nitro-4-trifluoromethylbenzene)propionitrile.

We claim:

1. A process which comprises reacting an o-fluoronitrobenzene bearing at least one innocuous ar-substituent and having an unsubstituted position para to the nitro group with an alpha-haloacetonitrile corresponding to the formula:

wherein L is halo and R is an alkyl group containing 1–10 carbons in an inert dipolar aprotic solvent and in the presence of a strong alkali metal compound base so that the nitrile undergoes a nucleophilic substitution on an unsubstituted ring carbon of the fluoronitrobenzene during which the alpha-halo substituent functions as a leaving group, thereby forming a fluoronitroarylacetonitrile.

2. The process of claim 1 wherein the fluoronitrobenzene is a fluoropolynitrobenzene.

3. The process of claim 2 wherein the fluoropolynitrobenzene is a polyfluoropolynitrobenzene.

4. The process of claim 1 wherein the fluoronitrobenzene is a fluoronitroalkylbenzene.

5. The process of claim 4 wherein the fluoronitroalkylbenzene is a fluoronitrotoluene.

6. The process of claim 1 wherein the alpha-haloacetonitrile is an alpha-halopropionitrile.

7. The process of claim 6 wherein the alpha-halopropionitrile is an alpha-chloro- or alpha-bromopropionitrile.

8. The process of claim 1 wherein the base is an alkali metal hydride.

9. The process of claim 8 wherein the base is sodium hydride or potassium hydride.

10. The process of claim 1 wherein the fluoronitroarylacetonitrile formed by the reaction is subsequently reduced to an aminofluoroarylacetonitrile.

11. The process of claim 1 wherein the fluoronitroarylacetonitrile formed by the reaction is subsequently hydrolyzed to a fluoronitroarylacetic acid.